United States Patent
Kobayashi et al.

(10) Patent No.: US 10,370,532 B2
(45) Date of Patent: Aug. 6, 2019

(54) RESIN COMPOSITION, BACKING MATERIAL FOR ULTRASONIC VIBRATOR, ULTRASONIC VIBRATOR, AND ULTRASONIC ENDOSCOPE

(71) Applicant: OLYMPUS CORPORATION, Hachioji-shi, Tokyo (JP)

(72) Inventors: Koji Kobayashi, Tokyo (JP); Takae Hayashi, Tokyo (JP); Kunihisa Obi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 405 days.

(21) Appl. No.: 15/271,714

(22) Filed: Sep. 21, 2016

(65) Prior Publication Data

US 2017/0009072 A1 Jan. 12, 2017

Related U.S. Application Data

(63) Continuation of application No. PCT/JP2015/056423, filed on Mar. 4, 2015.

(30) Foreign Application Priority Data

Apr. 14, 2014 (JP) .................. 2014-083180

(51) Int. Cl.
*B32B 27/38* (2006.01)
*H04R 17/00* (2006.01)
(Continued)

(52) U.S. Cl.
CPC ............... *C08L 63/00* (2013.01); *A61B 8/12* (2013.01); *A61B 8/4444* (2013.01);
(Continued)

(58) Field of Classification Search
None
See application file for complete search history.

(56) References Cited

U.S. PATENT DOCUMENTS

2005/0043625 A1* 2/2005 Oliver .................. G10K 11/002
600/459
2007/0029682 A1 2/2007 Aoki et al.
(Continued)

FOREIGN PATENT DOCUMENTS

CN 1908065 A 2/2007
CN 101325241 A 12/2008
(Continued)

OTHER PUBLICATIONS

Machine translation of SU-1682367-A1 (no date).*
(Continued)

*Primary Examiner* — Michael J Feely
(74) *Attorney, Agent, or Firm* — Holtz, Holtz & Volek PC

(57) ABSTRACT

A resin composition of the present invention contains: an epoxy resin (A); a hardener (B); and an ion exchanger (C). At least one of the epoxy resin (A) and the hardener (B) contains a modified silicone (S), and the epoxy resin (A) is at least one type selected from the group consisting of a bisphenol A type epoxy resin, a bisphenol F type epoxy resin, a phenol novolac type epoxy resin, and an epoxy-modified silicone.

8 Claims, 3 Drawing Sheets

(51) Int. Cl.

| | | |
|---|---|---|
| *A61B 8/12* | (2006.01) | |
| *C08L 63/00* | (2006.01) | |
| *C08L 63/04* | (2006.01) | |
| *C08L 83/06* | (2006.01) | |
| *C08G 59/24* | (2006.01) | |
| *C08G 59/30* | (2006.01) | |
| *C08G 59/40* | (2006.01) | |
| *C08G 59/50* | (2006.01) | |
| *A61B 8/00* | (2006.01) | |
| *C08K 3/22* | (2006.01) | |
| *C08K 5/16* | (2006.01) | |
| *C08L 63/02* | (2006.01) | |
| *C08G 77/14* | (2006.01) | |

(52) U.S. Cl.
CPC ......... *C08G 59/245* (2013.01); *C08G 59/306* (2013.01); *C08G 59/4085* (2013.01); *C08G 59/5033* (2013.01); *C08K 3/22* (2013.01); *C08K 5/16* (2013.01); *C08L 63/04* (2013.01); *C08L 83/06* (2013.01); *H04R 17/00* (2013.01); *C08G 77/14* (2013.01); *C08K 2003/2227* (2013.01)

(56) References Cited

U.S. PATENT DOCUMENTS

| | | |
|---|---|---|
| 2007/0282204 A1 | 12/2007 | Yamashita et al. |
| 2008/0312537 A1 | 12/2008 | Hiroaki |
| 2009/0273070 A1* | 11/2009 | Tendou ................ C08G 59/063 257/687 |

FOREIGN PATENT DOCUMENTS

| | | | |
|---|---|---|---|
| JP | 11252695 A | 9/1999 | |
| JP | 2001149373 A | 6/2001 | |
| JP | 2004358006 A | 12/2004 | |
| JP | 2012034160 A | 2/2012 | |
| SU | 1682367 A1 * | 10/1991 | ............... C08K 3/08 |

OTHER PUBLICATIONS

Derwent abstract of SU-1682367-A1 (no date).*
Chinese Office Action (and English language translation thereof) dated Jun. 25, 2018 issued in Chinese Application No. 201580018720.3.
Japanese Office Action dated Sep. 12, 2017 issued in counterpart Japanese Application No. JP 2014-083180.
Japanese Office Action (Notice of Allowance) (and English translation thereof) dated Nov. 7, 2017, issued in counterpart Japanese Application No. 2014-083180.
International Search Report (ISR) and Written Opinion dated Apr. 28, 2015 issued in International Application No. PCT/JP2015/056423.

* cited by examiner

RESIN COMPOSITION, BACKING MATERIAL FOR ULTRASONIC VIBRATOR, ULTRASONIC VIBRATOR, AND ULTRASONIC ENDOSCOPE

This application is a continuation application based on a PCT International Application No. PCT/JP2015/056423, filed on Mar. 4, 2015, whose priority is claimed on Japanese Patent Application No. 2014-83180, filed Apr. 14, 2014. Both of the content of the PCT International Application and the Japanese Application are incorporated herein by reference.

BACKGROUND OF THE INVENTION

Field of the Invention

The present invention relates to a resin composition, backing material for an ultrasonic vibrator, an ultrasonic vibrator, and an ultrasonic endoscope.

Description of Related Art

An ultrasonic endoscope has been used to observe an internal body for inspection and diagnosis. The ultrasonic endoscope includes an insertion portion inserted into the body, and an operation portion connected to the proximal end side of the insertion portion. An ultrasonic vibrator is provided at the distal end of the insertion portion.

The ultrasonic vibrator is schematically constituted by a piezoelectric element, a backing material provided on one surface of the piezoelectric element, and an acoustic matching layer and an acoustic lens which are provided on the other surface of the piezoelectric element. As described above, since the backing material is provided on one surface of the piezoelectric element, mechanical strength and the like are imparted to the ultrasonic vibrator. In addition, redundant vibration added to the ultrasonic endoscope is suppressed, and thus the acoustic characteristics of the ultrasonic endoscope change.

For example, Japanese Unexamined Patent Application, First Publication No. H11-252695 discloses a backing material formed of a rubber molded product having a specific hardness and a specific gravity, and a probe head and an ultrasonic diagnostic device which use a piezoelectric element fixed to the backing material. In the backing material of Japanese Unexamined Patent Application, First Publication No. H11-252695, mechanical strength and acoustic characteristics are improved.

An ultrasonic endoscope inserted into the body is subjected to a sterilization process under a high-temperature, high-pressure steam using an autoclave, or to a sterilization process using a chemical such as peracetic acid or gas (for example, hydrogen peroxide-based gas or ethylene oxide gas) before use.

However, since the ultrasonic endoscope is subjected to a sterilization process using the autoclave or the sterilization process using the chemical, there is a problem in that a disturbance occurs in an image obtained using the ultrasonic endoscope during inspection and diagnosis compared to that before the sterilization process. The disturbance in the image is caused by the deterioration of an organic material forming the ultrasonic vibrator due to the sterilization process.

There is a problem in that a bonded portion, which is a portion formed through bonding among the portions constituting the ultrasonic endoscope, is likely to be deteriorated when the ultrasonic endoscope is subjected to the sterilization process. For this, in order to limit the deterioration of a bonded portion of an endoscope during the sterilization process, for example, Japanese Unexamined Patent Application, First Publication No. 2004-358006 discloses a method of causing a specific filler to diffuse in a bonded layer that forms the bonded portion.

As a sterilization process for a medical device such as an endoscope, in the related art, a sterilization process using an autoclave or a sterilization process using ethylene oxide gas has been widely performed. However, in a case where an autoclave is used for a sterilization process of a medical device, there is a problem of thermal deterioration in the medical device. In a case where ethylene oxide gas is used for a sterilization process of a medical device, an effect on the human body of residual gas that remains in the medical device after the sterilization process causes a problem.

From this point of view, as the next sterilization process method, a sterilization process using hydrogen peroxide-based gas has attracted attention.

SUMMARY OF THE INVENTION

In order to solve the problems and achieve the associated object, the present invention employs the following means.

According to a first aspect of the present invention, a resin composition contains: an epoxy resin (A); a hardener (B); and an ion exchanger (C). At least one of the epoxy resin (A) and the hardener (B) contains a modified silicone (S), and the epoxy resin (A) is at least one type selected from the group consisting of a bisphenol A type epoxy resin, a bisphenol F type epoxy resin, a phenol novolac type epoxy resin, and an epoxy-modified silicone.

According to a second aspect of the present invention, in the resin composition of the first aspect, an amount of the modified silicone (S) may be 10 mass % or more with respect to a total amount of the epoxy resin (A) and the hardener (B).

According to a third aspect of the present invention, in the resin composition of the first or second aspect, a weight average molecular weight of the modified silicone (S) may be 500 to 50000.

According to a fourth aspect of the present invention, in the resin composition of any one of the first to third aspects, an amount of the ion exchanger (C) may be 0.25 to 10 parts by mass with respect to 100 parts by mass of a sum of the epoxy resin (A) and the hardener (B).

According to a fifth aspect of the present invention, a backing material for an ultrasonic vibrator is obtained by heating and molding the resin composition of any one of the first to fourth aspects.

According to a sixth aspect of the present invention, an ultrasonic vibrator includes: a piezoelectric element; the backing material for an ultrasonic vibrator of the fifth aspect, provided to be in contact with one surface of the piezoelectric element; an acoustic matching layer which has a first surface and a second surface, the first surface coming into contact with the other surface of the piezoelectric element and the backing material; and an acoustic lens provided to be in contact with the second surface of the acoustic matching layer.

According to a seventh aspect of the present invention, an ultrasonic endoscope includes: an insertion portion which is inserted into a body and is provided with the ultrasonic vibrator of the sixth aspect; an operation portion connected to a proximal end of the insertion portion; and a universal cord extending from the operation portion.

DETAILED DESCRIPTION OF THE INVENTION

<Resin Composition>

Figure 1:
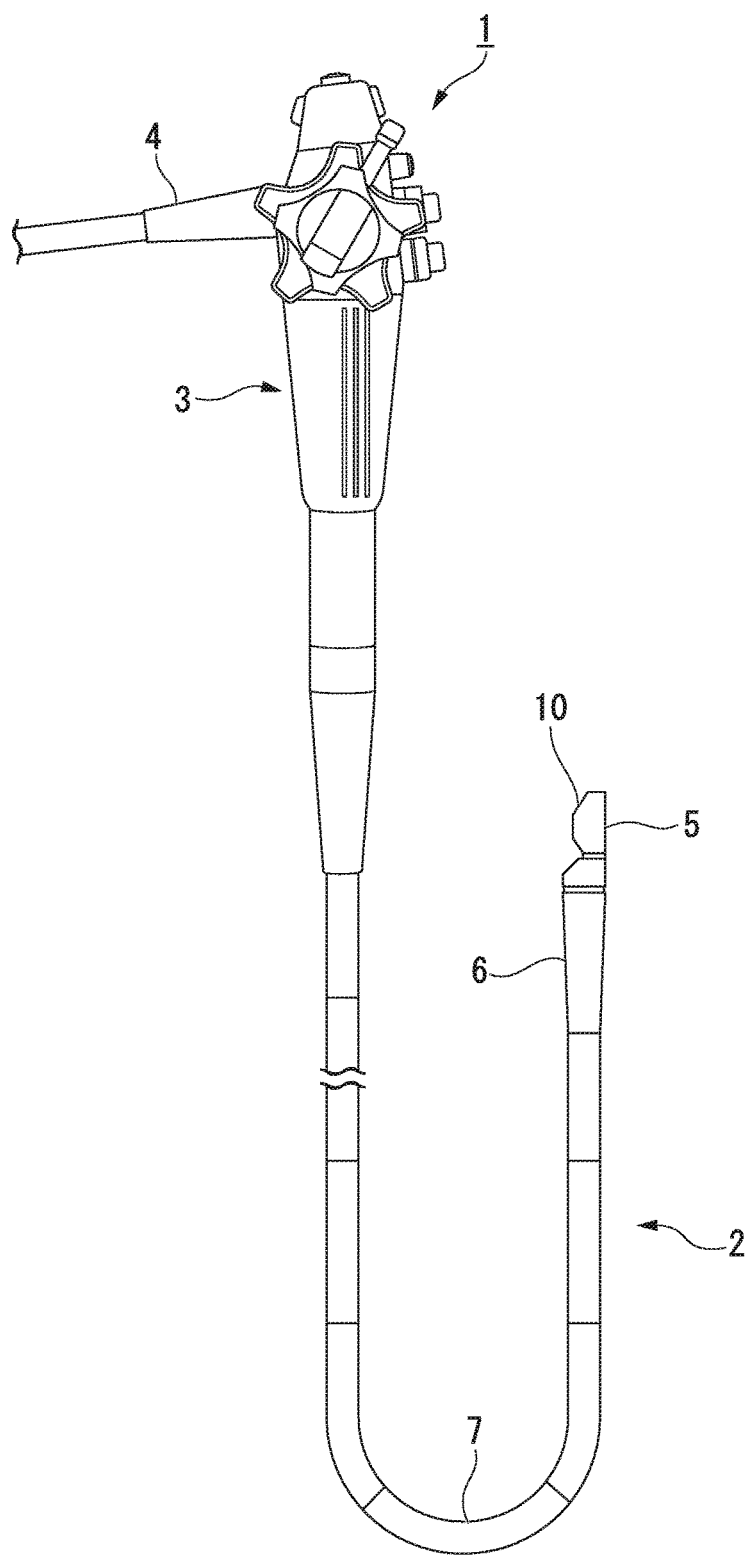
FIG. 1 is a plan view showing an embodiment of an ultrasonic endoscope.

A resin composition of the present invention is used for a backing material for an ultrasonic vibrator (hereinafter, also simply referred to as "backing material"), and contains an epoxy resin (A), a hardener (B), and an ion exchanger (C). Hereinafter, the epoxy resin (A), the hardener (B), and the ion exchanger (C) are also referred to as an (A) component, a (B) component, and a (C) component, respectively.

The resin composition containing the (A) component, the (B) component, and the (C) component is cured as a chemical reaction proceeds during heating. Accordingly, a cured material is formed, and a backing material molded.

(Epoxy Resin (A))

As the (A) component, at least one type of epoxy resin selected from the group consisting of a bisphenol A type epoxy resin, a bisphenol F type epoxy resin, a phenol novolac type epoxy resin, and an epoxy-modified silicone is used. Among these, the epoxy-modified silicone has excellent acoustic characteristics and sterilization resistance. Therefore, it is preferable that the epoxy-modified silicone is used as the (A) component.

As the bisphenol A type epoxy resin, for example, EPI-CLON (registered trademark) 840 (manufactured by DIC corporation), jER (registered trademark) 828 (manufactured by Mitsubishi Chemical Corporation), and the like may be used.

As the bisphenol F type epoxy resin, for example, EPI-CLON (registered trademark) 830 (manufactured by DIC corporation), jER (registered trademark) 807 (manufactured by Mitsubishi Chemical Corporation), and the like may be used.

As the phenol novolac type epoxy resin, for example, YDPN-638 (manufactured by Nippon Steel & Sumikin Chemical Co., Ltd.), N-770 (manufactured by DIC corporation), and the like may be used.

As the epoxy-modified silicone, for example, BY-16-855 (manufactured by Dow Corning Toray Co., Ltd.), X-22-9002 (manufactured by Shin-Etsu Chemical Co., Ltd.), SF8413 (manufactured by Dow Corning Toray Co., Ltd.), BY16-839 (manufactured by Dow Corning Toray Co., Ltd.), and the like may be used.

In the present invention, a polysiloxane into which an epoxy group or a substituent including an epoxy group is introduced as an organic group is referred to as an epoxy-modified silicone.

(Hardener (B))

As the (B) component, for example, an amine-based hardener, a polyamide resin, imidazoles, anhydrides, and the like may be used. Among these, by using the amine-based hardener, the rate of reaction with the (A) component can be further increased. Therefore, it is preferable that the amine-based hardener is used as the (B) component.

As the amine-based hardener, meta-xylylenediamine or a derivative thereof, an amine-modified silicone, and the like may be employed.

Examples of the derivative of meta-xylylenediamine include an alkylene oxide adduct, a glycidyl ester adduct, a glycidyl ether adduct, a Mannich adduct, an acrylonitrile adduct, an epichlorohydrin adduct, and a xylylenediamine trimer.

As the amine-modified silicone, for example, SF8417 (manufactured by Dow Corning Toray Co., Ltd.), WR301 (manufactured by Wacker Asahikasei Silicone Co., Ltd.), FZ-3785 (manufactured by Dow Corning Toray Co., Ltd.), and the like may be used.

In the present invention, a polysiloxane into which an amino group as an organic group, or a substituent including an amino group is introduced is referred to as an amine-modified silicone.

As the (B) component, one type may be singly used, or two or more types may be used in combination.

In the resin composition, it is preferable that the mixing ratio between the (A) component and the (B) component is set such that an epoxy group of the (A) component reacts with an equivalent amount of a functional group (an amino group or the like) of the (B) component which reacts with the epoxy group.

Here, a molecular weight per one functional group in the (A) component is referred to as an epoxy equivalent. In addition, a molecular weight per one functional group in a case where the amine-based hardener is used as the (B) component is referred to as an amine equivalent.

It is preferable that after calculating a theoretical mixing ratio from the epoxy equivalent in the (A) component and the amine equivalent in the (B) component, the mixing ratio between the (A) component and the (B) component is set in consideration of sterilization resistance and acoustic characteristics. Specifically, the mixing ratio (mass ratio) between the (A) component and the (B) component is preferably (A) component:(B) component=10:5 to 5:10, and more preferably 10:7 to 7:10.

When the mixing ratio between the (A) component and the (B) component is in the preferable range, one or more of the following can be easily suppressed: oxidization deterioration, softening deterioration due to hydrolysis and heat, hardening deterioration, brittle fracture, a reduction in adhesion strength in the backing material.

In the resin composition, at least one of the (A) component and the (B) component contains a modified silicone (S) (hereinafter, also referred to as (S) component). The (S) component may be contained in the (A) component, may be contained in the (B) component, and may be contained in both the (A) component and the (B) component.

Examples of the resin composition include: a resin composition containing the (A) component that contains an epoxy-modified silicone and the (B) component that does not contain the (S) component; a resin composition containing the (A) component that does not contain the (S) component and the (B) component that contains an amine-modified silicone; and a resin composition containing the (A) component that contains an epoxy-modified silicone and the (B) component that contains an amine-modified silicone.

Among these, the resin composition containing the (A) component that contains an epoxy-modified silicone and the (B) component that does not contain the (S) component is preferable because the effects of the present invention can be particularly easily obtained. Among these, it is more preferable that the (A) component contains only an epoxy-modified silicone.

The weight average molecular weight (Mw) of the (S) component is preferably 500 to 50000, and more preferably 10000 to 50000. When the Mw of the (S) component is equal to or higher than the preferable lower limit, sterilization resistance is further improved. When the Mw is equal to or lower than the preferable upper limit, acoustic characteristics are further improved. Furthermore, when the Mw is equal to or lower than the preferable upper limit, moldability is further improved when an ultrasonic vibrator is produced.

The weight average molecular weight (Mw) in the present invention means a measurement value of a molecular weight obtained by performing gel permeation chromatography (GPC) using polystyrene as a standard sample.

The amount of the (S) component contained in the resin composition is preferably 10 mass % or more with respect to the total amount (100 mass %) of the (A) component and the (B) component, more preferably 20 mass % or more, even more preferably 40 mass % or more, and particularly preferably 50 mass % or more, and may also be 100 mass %. When the amount of the (S) component is equal to or higher than the preferable lower limit, sterilization resistance and acoustic characteristics are further improved.

(Ion Exchanger (C))

In the present invention, the ion exchanger contains a material which has a functional group that acts during an ion exchange in a molecule and performs the ion exchange to adsorb or separate metal ions, chloride ions, and the like.

The ion exchange performed by the (C) component may be any of a cation exchange, an anion exchange, or both the ion exchanges. As the (C) component, any of an organic ion exchanger and an inorganic ion exchanger may be used.

As the organic ion exchanger, an ion-exchange resin, an ion-exchange cellulose, or the like may be employed.

As the inorganic ion exchanger, a material which performs a cation exchange such as a zirconium compound, an antimony compound, zeolites, and clay minerals; a material which performs an anion exchange such as a bismuth compound, a magnesium compound, an aluminum compound, hydrotalcite, and a zirconium compound; or a combination thereof may be employed.

The zirconium compound means a compound containing zirconium Similarly, the antimony compound, the bismuth compound, the magnesium compound, and the aluminum compound mean compounds respectively containing antimony, bismuth, magnesium, and aluminum in their molecules.

As the (C) component, one type may be singly used, or two or more types may be used in combination.

Among these, when an inorganic ion exchanger is used as the (C) component, sterilization resistance is further improved. Therefore, as the (C) component, an inorganic ion exchanger is preferable. Among the inorganic ion exchangers, at least one type selected from the group consisting of the zirconium compound, the antimony compound, the bismuth compound, the magnesium compound, and the aluminum compound is preferable. As the (C) component, at least one type selected from the group consisting of the zirconium compound, the antimony compound, and the bismuth compound is more preferable. As the (C) component, at least one type selected from the group consisting of the antimony compound and the bismuth compound is even more preferable. As the (C) component, the bismuth compound is particularly preferably used.

As the (C) component, for example, an ion-trapping agent IXE (registered trademark) manufactured by Toagosei Co., Ltd. can be appropriately used. More specifically, IXE-100 (zirconium compound) and IXE-300 (antimony compound) which perform a cation exchange; IXE-500 (bismuth compound), IXE-530 (bismuth compound), IXE-550 (bismuth compound), IXE-700F (a combination of a magnesium compound and an aluminum compound), and IXE-800 (zirconium compound) which perform an anion exchange; and IXE-600 (a combination of an antimony compound and a bismuth compound) and IXE-633 (a combination of an antimony compound and a bismuth compound) which perform both a cation exchange and an anion exchange may be employed.

The amount of the (C) component contained in the resin composition is preferably 0.25 to 10 parts by mass with respect to 100 parts by mass of the sum of the (A) component and the (B) component, and more preferably 0.5 to 5 parts by mass. When the amount of the (C) component is in the preferable range, sterilization resistance is further improved. Furthermore, when the amount thereof is equal to or higher than the preferable lower limit, sterilization resistance is further improved. When the amount thereof is equal to or lower than the preferable upper limit, moldability is further improved when an ultrasonic vibrator is produced.

(Other Components)

The resin composition of the present invention may contain other components in addition to the (A) component, the (B) component, and the (C) component described above. Examples of the other components include a filler.

As the filler that may be used in the resin composition, metal oxides such as alumina, silica, magnesium oxide, and oxides of zirconium; and rubbers such as silicone rubber, acrylic rubber, and butadiene rubber may be employed.

Since a metal oxide is contained as the filler of the resin composition, the density of the backing material is increased when the backing material is molded by heating the resin composition. Furthermore, since the metal oxide is used in the resin composition, the acoustic impedance (obtained by the product of the density and the speed of sound) of the backing material is increased when the backing material is molded by heating the resin composition. Accordingly, vibration of the piezoelectric element is efficiently transmitted to the backing material.

Since the metal oxide functions as an ultrasonic scatterer, when the metal oxide is used in the resin composition, an attenuation factor in ultrasounds increases.

As the filler, one type may be singly used, or two or more types may be used in combination.

As the filler of the metal oxides, alumina is preferable, and as the filler of the rubbers, acrylic rubber is preferable.

By using alumina as the filler, resistance to the sterilization process using a chemical increases. Accordingly, the adhesion strength between the piezoelectric element and the backing material is more properly maintained before and after the sterilization process.

By using acrylic rubber as the filler, a cross-link density is increased when the cured material is formed by heating the resin composition. Accordingly, resistance to the sterilization process using an autoclave and resistance to the sterilization process using a chemical are further improved.

In the resin composition, in addition to the above-described components, an epoxy resin other than the (A) component, such as a brominated epoxy resin, an alicyclic epoxy resin, and a polyfunctional epoxy resin; and additives such as catalysts, adhesion imparting agents, solvents, plasticizers, antioxidants, polymerization inhibitors, surfactants, fungicides, and colorant may be used.

(Operational Effects)

The resin composition of the present invention described above contains at least one type of epoxy resin (A) selected from the group consisting of a bisphenol A type epoxy resin, a bisphenol F type epoxy resin, a phenol novolac type epoxy resin, and an epoxy-modified silicone, the hardener (B), and the ion exchanger (C), and the modified silicone (S) is contained in at least one of the (A) component and the (B) component.

Since the resin composition contains the (S) component, the cured material formed by heating the resin composition contains a silicone backbone in its structure.

The silicone backbone is a structure formed by repeating —Si—O— and has a high binding energy. Therefore, even when the sterilization process is performed on the cured material, it is difficult to break bonds in the cured material.

Since the cured material has the silicone backbone, the cured material exhibits appropriately low elasticity. Accordingly, when vibration is applied to the ultrasonic vibrator provided with the backing material molded using the cured material, additional vibration can be limited.

Since the resin composition contains the (C) component, metal ions, chloride ion, and the like, which are present in the resin composition, are adsorbed onto the (C) component. Therefore, in the cured material formed by heating the resin composition, the amount of metal ions, chloride ions, and the like in a free state is small. Accordingly, when the sterilization process is performed on the cured material, deterioration of the cured material due to the actions of metal ions, chloride ions, and the like is less likely to occur.

As described above, according to the resin composition of the present invention, a backing material for an ultrasonic vibrator, which exhibits both of excellent sterilization resistance and good acoustic characteristics can be provided.

The cured material formed of the resin composition of the present invention is less likely to undergo thermal deterioration during the sterilization process using an autoclave. In addition, the cured material has high resistance to chemicals such as peracetic acid and gases.

Among these, the resin composition of the present invention has particularly high resistance to a gas-based sterilization process such as a hydrogen peroxide plasma sterilization process. Therefore, the resin composition of the present invention is effective in a gas-based sterilization process such as a hydrogen peroxide plasma sterilization process.

<Backing Material for Ultrasonic Vibrator, Ultrasonic Vibrator, and Ultrasonic Endoscope>

The resin composition of the present invention described above is particularly appropriate as the material of the backing material for an ultrasonic vibrator.

The backing material which uses the resin composition is appropriate for an ultrasonic vibrator. The ultrasonic vibrator having the backing material is appropriate for an ultrasonic endoscope.

The ultrasonic vibrator having the backing material using the resin composition of the present invention, and the ultrasonic endoscope having the ultrasonic vibrator will be described in detail with reference to FIGS. 1 to 3.

FIG. 1 shows an embodiment of the ultrasonic endoscope of the present invention.

An ultrasonic endoscope 1 of this embodiment is constituted by a long, thin insertion portion 2 inserted into the body, an operation portion 3 connected to the proximal end of the insertion portion 2, and a universal cord 4 that extends from the operation portion 3.

In the insertion portion 2, from the distal end thereof, a distal end hard portion 5 provided with an ultrasonic vibrator 10, a bendable portion 6 which is bendable, and a flexible pipe 7 which is long and has a small diameter and flexibility are connected in this order.

The ultrasonic vibrator 10 is provided with the backing material which uses the resin composition of the present invention described above.

Figure 2:
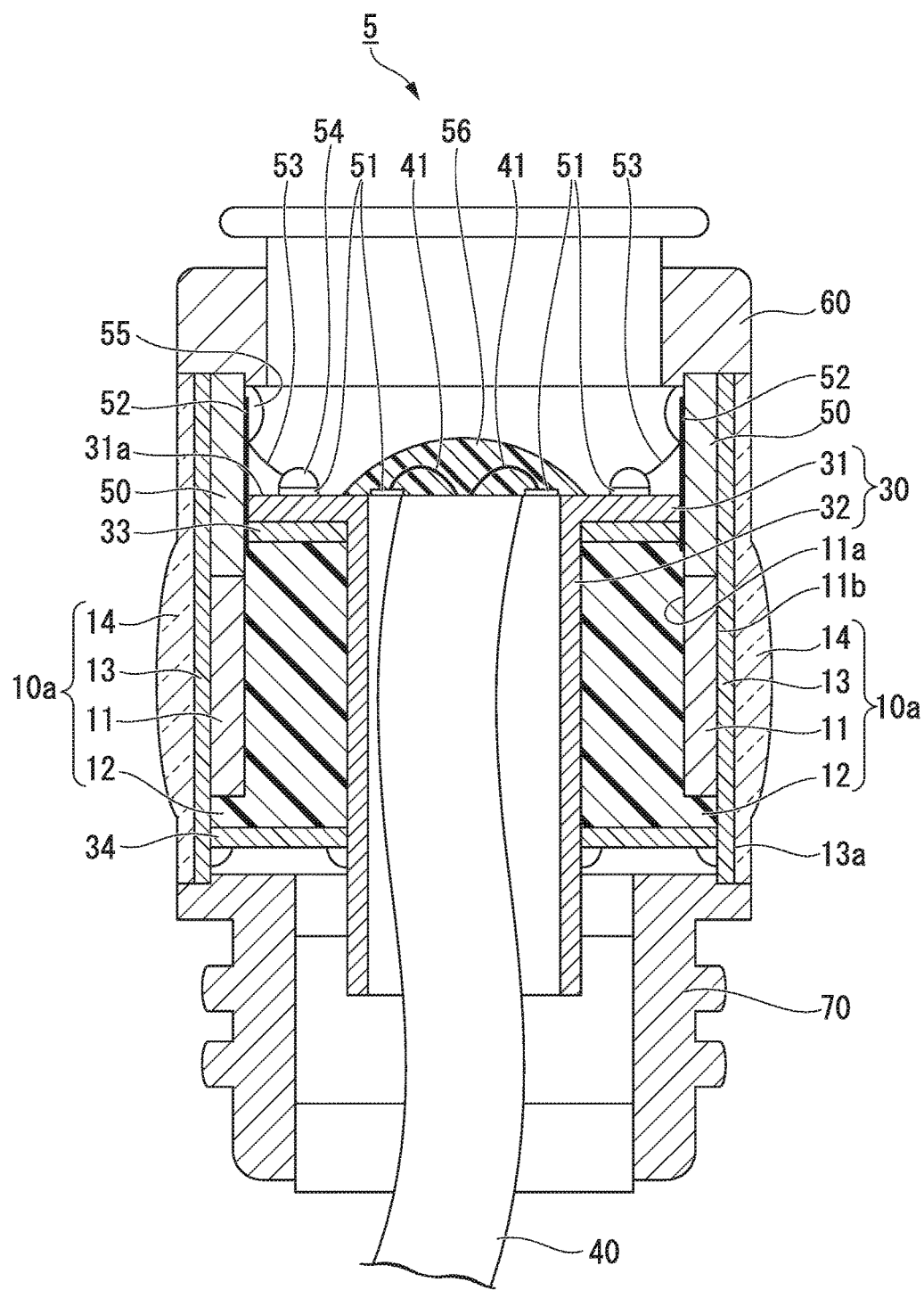
FIG. 2 is a sectional view showing an embodiment of a distal end hard portion in the ultrasonic endoscope shown in FIG. 1.

FIG. 2 shows an embodiment of the distal end hard portion in the ultrasonic endoscope shown in FIG. 1.

The distal end hard portion 5 of this embodiment includes a cylindrical member 30 which accommodates a coaxial cable 40, a plurality of ultrasonic vibrators 10a (first embodiment) which are arranged in a circumferential direction along the circumferential surface of the cylindrical member 30, and a pair of annular members 33 and 34 which are separated from each other to have the cylindrical member 30 inserted therethrough.

The ultrasonic vibrator 10a includes a flat plate-shaped piezoelectric element 11, a backing material 12, an acoustic matching layer 13, an acoustic lens 14, and an electrode (not shown).

The backing material 12 is provided on the side of a surface 11a of the piezoelectric element 11 in a direction of the cylindrical member 30 to be in contact with the surface 11a. In addition, the backing material 12 is in contact with a portion of a surface 11b which is a surface of the piezoelectric element 11 with which the acoustic matching layer 13 is in contact.

The acoustic matching layer 13 and the acoustic lens 14 are provided on the side of the surface 11b of the piezoelectric element 11 in a direction opposite to the cylindrical member 30. The acoustic matching layer 13 is provided to be in contact with the surface 11b. The acoustic lens 14 is provided to be in contact with a surface 13a of the acoustic matching layer 13 in a direction opposite to the piezoelectric element 11.

The cylindrical member 30 is constituted by an annular flange 31, and a cylindrical portion 32 which extends from the edge of the center of the flange 31 in a direction toward the flexible pipe 7.

The annular member 33 is adjacent to the flange 31 and is attached to be in contact with a substrate 50 which extends from the piezoelectric element 11 in a direction toward the distal end of the distal end hard portion 5.

The annular member 34 is attached to be in contact with the acoustic matching layer 13 on a side closer to the flexible pipe 7 than the piezoelectric element 11.

On the surface 311a of the flange 31 in a direction opposite to the annular member 33, a number of electrode pads 51 are provided.

In FIG. 2, a wire 41 extending from the coaxial cable 40 is connected to the electrode pad 51. The electrode pad 51 and an electrode layer 52 provided on the substrate 50 are connected by a wire 53. The electrode pad 51 and the wire 53 are bonded to each other by a solder 54, and the electrode layer 52 and the wire 53 are bonded to each other by a solder 55.

The entirety of wire connection portions between the electrode pads 51 and the wires 41 are coated with a potting resin 56 so as to prevent the wires 41 from being detached from the electrode pads 51, for example, under a load applied to the coaxial cable 40.

The distal end of the distal end hard portion 5 is provided with a distal end structure member 60 to block the wire connection portions between the electrode pads 51 and the wires 41. The distal end hard portion 5 is connected to the bendable portion 6 via a connection member 70.

In the distal end hard portion 5 of this embodiment, the ultrasonic vibrator 10a is produced, for example, in the following manner (refer to Japanese Unexamined Patent Application, First Publication No. 2007-151562).

First, the acoustic matching layer 13 is formed. Separately from this, the piezoelectric element 11 in which the electrodes (not shown) are respectively provided at the surfaces 11a and 11b is produced. Next, the acoustic matching layer 13, and the piezoelectric element 11 having the electrodes (not shown) at the surfaces 11a and 11b are bonded to each other.

In the distal end hard portion 5 of this embodiment, the substrate 50 is attached to the piezoelectric element 11 to extend in a planar direction. Each of the annular members 33 and 34 is attached at a predetermined position.

Next, the resin composition of the present invention is caused to flow between the piezoelectric element 11 and the cylindrical member 30 to fill a space between the annular member 33 and the annular member 34. The backing material 12 is molded by heating and curing the resin composition. The backing material 12 is in contact with the surface 11a of the piezoelectric element 11 and also is in contact with a portion of the acoustic matching layer 13.

Next, the acoustic lens 14 is formed on the surface 13a of the acoustic matching layer 13 in the direction opposite to the piezoelectric element 11, thereby producing the ultrasonic vibrator 10a.

Figure 3:
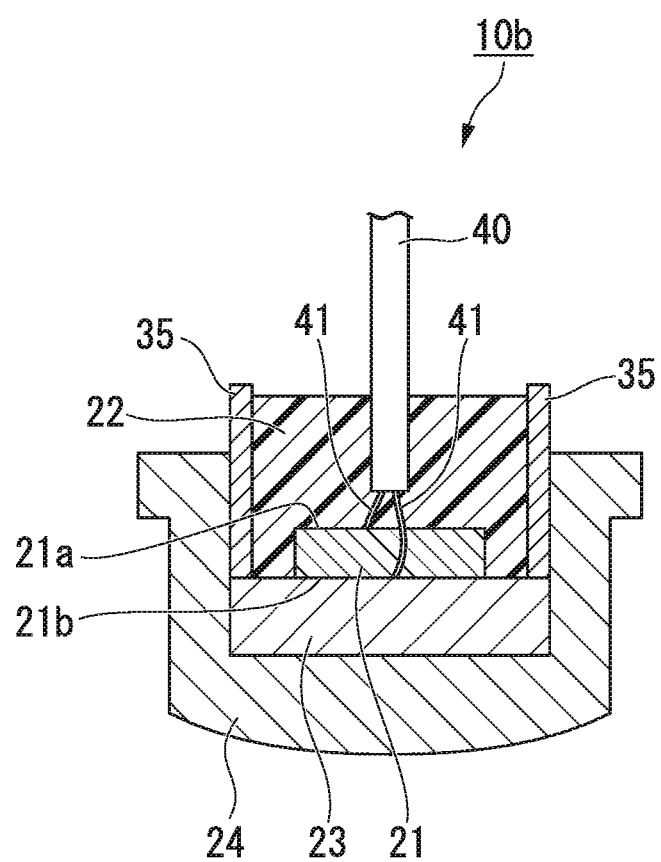
FIG. 3 is a sectional view showing another embodiment of an ultrasonic vibrator.

The ultrasonic vibrator 10 provided in the distal end hard portion 5 in the ultrasonic endoscope shown in FIG. 1 is not limited to the ultrasonic vibrator 10a described above, and an embodiment (second embodiment) shown in FIG. 3 may also be employed.

An ultrasonic vibrator 10b of the second embodiment shown in FIG. 3 includes a disk-shaped piezoelectric element 21, a backing material 22 provided on one surface 21a side of the piezoelectric element 21, an acoustic matching layer 23 provided on the other surface 21b side of the piezoelectric element 21, an acoustic lens 24 at the outermost layer, and electrodes (not shown) provided on the surfaces 21a and 21b on both sides of the piezoelectric element 21.

In FIG. 3, to the electrodes (not shown) respectively provided at the surfaces 21a and 21b of the piezoelectric element 21, wires 41 extending from a coaxial cable 40 are connected.

The ultrasonic vibrator 10b of the second embodiment can be produced by a well-known method. For example, the piezoelectric element 21 in which the electrodes (not shown) are respectively provided at the surfaces 21a and 21b and the acoustic matching layer 23 are bonded to each other.

Next, the resin composition of the present invention is caused to flow into a space between the acoustic matching layer 23 and a mold member 35 provided upright from the circumferential edge of the acoustic matching layer 23. The backing material 22 is molded by heating and curing the resin composition.

Next, the acoustic lens 24 is formed at the outermost layer, thereby producing the ultrasonic vibrator 10b of the second embodiment.

The ultrasonic vibrator 10a of the first embodiment and the ultrasonic vibrator 10b of the second embodiment described above include the backing material formed by using the resin composition of the present invention. Therefore, the ultrasonic vibrator 10a and the ultrasonic vibrator 10b have excellent resistance to the sterilization process. Furthermore, in ultrasonic endoscopes provided with the ultrasonic vibrator 10a and the ultrasonic vibrator 10b, even when the sterilization process is repeatedly performed, a disturbance in an image obtained during inspection and diagnosis is less likely to occur.

The ultrasonic vibrator 10a and the ultrasonic vibrator 10b have a large ultrasonic attenuation factor. As the attenuation factor of the ultrasonic vibrator in ultrasounds increases, unnecessary vibration can be efficiently suppressed. Therefore, as the attenuation factor of the ultrasonic vibrator in ultrasounds increases, it is possible to reduce the thickness of the backing material part.

That is, it is possible to reduce the thickness of the backing material of the ultrasonic vibrator by using the resin composition of the present invention, and thus a reduction in the size of the ultrasonic vibrator can be achieved. Therefore, the ultrasonic vibrator 10a and the ultrasonic vibrator 10b of the present invention are useful for ultrasonic endoscopes.

The resin composition of the present invention has good fluidity when heated. Therefore, when the ultrasonic vibrator 10a or the ultrasonic vibrator 10b is produced, the resin composition can be caused to fill a predetermined space without gaps. That is, by using the resin composition of the present invention, moldability is further improved when the ultrasonic vibrator is produced.

EXAMPLES

Hereinafter, the present invention will be described in further detail using Examples, but the present invention is not limited to Examples.

Components used in Examples will be described below.
Epoxy Resin (A)
Bisphenol A type epoxy resin: trade name "EPICLON (registered trademark) 840", manufactured by DIC corporation.
Bisphenol F type epoxy resin: trade name "EPICLON (registered trademark) 830", manufactured by DIC corporation.
Phenol novolac type epoxy resin: trade name "YDPN-638", manufactured by Nippon Steel & Sumikin Chemical Co., Ltd.
Epoxy-modified silicone (Mw500): weight average molecular weight 500, trade name "BY-16-855", manufactured by Dow Corning Toray Co., Ltd.
Epoxy-modified silicone (Mw10000): weight average molecular weight 10000, trade name "X-22-9002", manufactured by Shin-Etsu Chemical Co., Ltd.
Epoxy-modified silicone (Mw50000): weight average molecular weight 50000, synthetic product.
Epoxy-modified silicone (Mw100000): weight average molecular weight 100000, synthetic product.
Hardener (B)
Meta-xylylenediamine: amine-based hardener, trade name "MXDA", manufactured by Mitsubishi Gas Chemical Company, Inc.
Amine-modified silicone (Mw500): weight average molecular weight 500, "SF8417", manufactured by Dow Corning Toray Co., Ltd.
Ion Exchanger (C)
Inorganic ion exchanger: trade name "IXE (registered trademark)-500", manufactured by Toagosei Co., Ltd.
Other Components
Alumina: filler, trade name "A-43M", manufactured by Showa Denko K. K.
Dimethyl silicone: trade name "KMP-597" (average particle size 5 μm), manufactured by Shin-Etsu Chemical Co., Ltd.
<Preparation of Resin Composition>
According to compositions (mixing components, amounts (expressed as parts by mass) in the resin composition) shown in Tables 1 and 2, a resin composition of each of Examples was prepared in the following manner.

The amount of a mixing component in Tables represents the amount of the pure mixing component. In a case where there are blanks in Tables, the corresponding mixing component is not mixed.

Examples 1 to 3

A resin composition was obtained by mixing together 10 parts by mass of an epoxy-modified silicone (Mw500), 10 parts by mass of meta-xylylenediamine, inorganic ion exchangers in predetermined amounts, and 25 parts by mass of alumina.

Examples 4 to 8

A resin composition was obtained by mixing together 10 parts by mass of an epoxy-modified silicone (Mw10000), 10 parts by mass of meta-xylylenediamine, inorganic ion exchangers in predetermined amounts, and 25 parts by mass of alumina.

Examples 9 to 11

A resin composition was obtained by mixing together 10 parts by mass of an epoxy-modified silicone (Mw50000), 10 parts by mass of meta-xylylenediamine, inorganic ion exchangers in predetermined amounts, and 25 parts by mass of alumina.

Example 12

A resin composition was obtained by mixing together 10 parts by mass of an epoxy-modified silicone (Mw500), 10 parts by mass of an amine-modified silicone Mw500), 0.5 parts by mass of an inorganic ion exchanger, and 25 parts by mass of alumina.

Example 13

A resin composition was obtained by mixing together 8 parts by mass of a bisphenol A type epoxy resin, 2 parts by mass of an epoxy-modified silicone (Mw500), 10 parts by mass of meta-xylylenediamine, 0.5 parts by mass of an inorganic ion exchanger, and 25 parts by mass of alumina.

Example 14

A resin composition was obtained by mixing together 8 parts by mass of a bisphenol F type epoxy resin, 2 parts by mass of an epoxy-modified silicone (Mw500), 10 parts by mass of meta-xylylenediamine, 0.5 parts by mass of an inorganic ion exchanger, and 25 parts by mass of alumina.

Example 15

A resin composition was obtained by mixing together 8 parts by mass of a phenol novolac type epoxy resin, 2 parts by mass of an epoxy-modified silicone (Mw500), 10 parts by mass of meta-xylylenediamine, 0.5 parts by mass of an inorganic ion exchanger, and 25 parts by mass of alumina.

Comparative Example 1

A resin composition was obtained by mixing together 10 parts by mass of a bisphenol A type epoxy resin, and 10 parts by mass of meta-xylylenediamine.

Comparative Example 2

A resin composition was obtained by mixing together 10 parts by mass of a bisphenol A type epoxy resin, 10 parts by mass of meta-xylylenediamine, and 25 parts by mass of alumina.

Comparative Example 3

A resin composition was obtained by mixing together 10 parts by mass of a bisphenol A type epoxy resin, 10 parts by mass of meta-xylylenediamine, 25 parts by mass of alumina, and 5 parts by mass of dimethyl silicone.

Comparative Example 4

A resin composition was obtained by mixing 8 together parts by mass of a bisphenol A type epoxy resin, 2 parts by mass of an epoxy-modified silicone (Mw500), 10 parts by mass of meta-xylylenediamine, and 25 parts by mass of alumina.

Comparative Example 5

A resin composition was obtained by mixing together 10 parts by mass of an epoxy-modified silicone (Mw500), 10 parts by mass of meta-xylylenediamine, and 25 parts by mass of alumina.

Comparative Example 6

A resin composition was obtained by mixing together 10 parts by mass of an epoxy-modified silicone (Mw500), 2 parts by mass of meta-xylylenediamine, 8 parts by mass of an amine-modified silicone (Mw500), and 25 parts by mass of alumina.

Comparative Example 7

A resin composition was obtained by mixing together 10 parts by mass of an epoxy-modified silicone (Mw500), 10 parts by mass of an amine-modified silicone (Mw500), and 25 parts by mass of alumina.

Comparative Example 8

A resin composition was obtained by mixing together 10 parts by mass of an epoxy-modified silicone (Mw10000), 10 parts by mass of meta-xylylenediamine, and 25 parts by mass of alumina.

Comparative Example 9

A resin composition was obtained by mixing together 10 parts by mass of an epoxy-modified silicone (Mw50000), 10 parts by mass of meta-xylylenediamine, and 25 parts by mass of alumina.

Comparative Example 10

A resin composition was obtained by mixing together 10 parts by mass of an epoxy-modified silicone (Mw100000), 10 parts by mass of meta-xylylenediamine, and 25 parts by mass of alumina.

Comparative Example 11

A resin composition was obtained by mixing together 10 parts by mass of a bisphenol A type epoxy resin, 10 parts by mass of meta-xylylenediamine, 0.5 parts by mass of an inorganic ion exchanger, and 25 parts by mass of alumina.

Comparative Example 12

A resin composition was obtained by mixing together 10 parts by mass of a bisphenol A type epoxy resin, 10 parts by mass of meta-xylylenediamine, 0.5 parts by mass of an inorganic ion exchanger, 25 parts by mass of alumina, and 5 parts by mass of dimethyl silicone.

<Production of Ultrasonic Vibrator>

An ultrasonic vibrator in the same form as that of the ultrasonic vibrator 10b of the second embodiment shown in FIG. 3 was produced according to a well-known production method using each of the resin composition of the examples.

The backing material 22 in the ultrasonic vibrator 10b was molded by causing the resin composition of each of the examples to flow into a predetermined space surrounded by the acoustic matching layer 23 and the mold member 35 so as to be cured.

<Evaluation>

[Evaluation of Sterilization Resistance]

1) Sterilization Process

The ultrasonic vibrator produced by using the resin composition of each of the examples was subjected to a sterilization process. As a method of the sterilization process, a gas sterilization method in which hydrogen peroxide-based gas was used in a low-temperature plasma sterilization device was used.

2) Measurement of Storage Elastic Modulus

The storage elastic modulus of the ultrasonic vibrator before and after the sterilization process was measured as follows.

A backing material having a longitudinal length of 10 mm, a transverse length of 30 mm, and a thickness of 1 mm was cut from the ultrasonic vibrator before and after the sterilization process as a measurement sample.

Using a dynamic viscoelasticity measuring device (Q800, manufactured by TA Instruments), the storage elastic modulus of the measurement sample in a predetermined measurement mode (tensile mode) under a predetermined temperature condition (−90° C. to 100° C.) was measured.

3) Evaluation of Sterilization Resistance

By substituting the measurement results of the storage elastic modulus into the following Expression (1), a reduction ratio of the storage elastic modulus was calculated. The results are shown in Tables 1 and 2.

$$\text{A reduction ratio (\%) of the storage elastic modulus} = (\text{the storage elastic modulus at 25° C. after the sterilization process/the storage elastic modulus at 25° C. before the sterilization process}) \times 100 \quad (1)$$

A lower value of the reduction ratio of the storage elastic modulus means higher sterilization resistance.

[Evaluation of Acoustic Characteristics]

In JIS Z 2354, a method of measuring an attenuation coefficient according to a water immersion multiple reflection method using a flat plate measurement piece having an arbitrary thickness is specified. Using the method based on the measurement method of the attenuation coefficient, the attenuation factor (%) of the ultrasonic vibrator produced using the resin composition of each of the examples at was measured a frequency of 5 MHz. The results are shown in Tables 1 and 2.

A higher value of the attenuation factor of the ultrasonic vibrator means excellent performance in suppressing unnecessary vibration and better acoustic characteristics of the ultrasonic vibrator.

[Evaluation of Moldability]

During the production of the ultrasonic vibrator, a state of the resin composition of each of the examples which flows into a predetermined space was observed, and the moldability thereof was evaluated.

For the evaluation, moldability was evaluated in two stages of good moldability (the predetermined space was filled with the resin composition without gaps) and poor moldability (there were portions where the predetermined space was not filled with the resin composition). The evaluation results are shown in Tables 1 and 2.

TABLE 1

| | | Examples | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| (A) component | Bisphenol A type epoxy resin | | | | | | | | | | | | 8 | | | |
| | Bisphenol F type epoxy resin | | | | | | | | | | | | | 8 | | |
| | Phenol novolac type epoxy resin | | | | | | | | | | | | | | | 8 |
| | Epoxy-modified silicone Mw500 | 10 | 10 | 10 | | | | | | | | | 10 | 2 | 2 | 2 |
| | Epoxy-modified silicone Mw10000 | | | | 10 | 10 | 10 | 10 | 10 | | | | | | | |
| | Epoxy-modified silicone Mw50000 | | | | | | | | | 10 | 10 | 10 | | | | |
| (B) component | Meta-xylylenediamine | 10 | 10 | 10 | 10 | 10 | 10 | 10 | 10 | 10 | 10 | 10 | | 10 | 10 | 10 |
| | Amine-modified silicone Mw500 | | | | | | | | | | | | 10 | | | |
| (C) component | Inorganic ion exchanger | 0.1 | 0.5 | 1 | 0.05 | 0.1 | 0.5 | 1 | 2 | 0.1 | 0.5 | 1 | 0.5 | 0.5 | 0.5 | 0.5 |
| Others | Alumina | 25 | 25 | 25 | 25 | 25 | 25 | 25 | 25 | 25 | 25 | 25 | 25 | 25 | 25 | 25 |
| Amount of modified silicone with respect to total amount of (A) component and (B) component | | 50 | 50 | 50 | 50 | 50 | 50 | 50 | 50 | 50 | 50 | 50 | 100 | 10 | 10 | 10 |
| Amount of (C) component (parts by mass) with respect to 100 parts by mass of sum of (A) component and (B) component | | 0.50 | 2.5 | 5.0 | 0.25 | 0.50 | 2.5 | 5.0 | 10 | 0.50 | 2.5 | 5.0 | 2.5 | 2.5 | 2.5 | 2.5 |

TABLE 1-continued

| | | Examples | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Evaluation | 10 | 5 | 10 | 20 | 10 | 5 | 10 | 20 | 5 | 2 | 5 | 5 | 10 | 10 | 10 | |
| | 37 | 37 | 37 | 37 | 37 | 37 | 37 | 37 | 37 | 37 | 37 | 37 | 40 | 37 | 37 | 37 |
| | Moldability | Good | Good | Good | Good | Good | Good | Poor | Good | Good | Good | Good | Good | Good | Good | Good |

TABLE 2

| | | Comparative Example | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| (A) component | Bisphenol A type epoxy resin | 10 | 10 | 10 | 8 | | | | | | | 10 | 10 |
| | Epoxy-modified silicone Mw500 | | | | 2 | 10 | 10 | 10 | | | | | |
| | Epoxy-modified silicone Mw10000 | | | | | | | | 10 | | | | |
| | Epoxy-modified silicone Mw50000 | | | | | | | | | 10 | | | |
| | Epoxy-modified silicone Mw100000 | | | | | | | | | | 10 | | |
| (B) component | Meta-xylylenediamine | 10 | 10 | 10 | 10 | 10 | 2 | | 10 | 10 | 10 | 10 | 10 |
| | Amine-modified silicone Mw500 | | | | | | 8 | 10 | | | | | |
| (C) component | Inorganic ion exchanger | | | | | | | | | | | 0.5 | 0.5 |
| Others | Alumina | | 25 | 25 | 25 | 25 | 25 | 25 | 25 | 25 | 25 | 25 | 25 |
| | Dimethyl silicone | | | 5 | | | | | | | | | 5 |
| Amount of modified silicone with respect to total amount of (A) component and (B) component | | 0 | 0 | 0 | 10 | 50 | 90 | 100 | 50 | 50 | 50 | 0 | 0 |
| Amount of (C) component (parts by mass) with respect to 100 parts by mass of sum of (A) component and (B) component | | 0 | 0 | 0 | 0 | 0 | 0 | 0 | 0 | 0 | 0 | 2.5 | 2.5 |
| Evaluation | Sterilization resistance [reduction ratio (%) of storage elastic modulus] | 80 | 80 | 80 | 40 | 40 | 40 | 40 | 30 | 25 | 25 | 20 | 20 |
| | Acoustic characteristics [attenuation factor (%)] | 5 | 20 | 20 | 27 | 30 | 33 | 34 | 37 | 40 | 40 | 20 | 25 |
| | Moldability | Good | Good | Good | Good | Good | Good | Good | Good | Good | Poor | Poor | Poor |

From Tables 1 and 2, it could be confirmed that the resin compositions of Examples 1 to 15 to which the present invention was applied have excellent sterilization resistance and good acoustic characteristics.

On the other hand, in the resin compositions of Comparative Examples 1 to 12 which are outside of the ranges of the present invention, at least one of sterilization resistance and acoustic characteristics was deteriorated.

What is claimed is:

1. An ultrasonic vibrator comprising:
a piezoelectric element;
a backing material provided to be in contact with a first surface of the piezoelectric element;
an acoustic matching layer which has a first surface and a second surface, the first surface provided to be in contact with a second surface of the piezoelectric element and the backing material; and
an acoustic lens provided to be in contact with the second surface of the acoustic matching layer,
wherein the backing material is obtained by heating and molding a resin composition that includes:
an epoxy resin (A);
a hardener (B); and
an ion exchanger (C),
wherein at least one of the epoxy resin (A) and the hardener (B) contains a modified silicone (S), and
wherein the epoxy resin (A) is at least one type selected from the group consisting of a bisphenol A type epoxy resin, a bisphenol F type epoxy resin, a phenol novolac type epoxy resin, and an epoxy-modified silicone.

2. The ultrasonic vibrator according to claim 1, wherein an amount of the modified silicone (S) is 10 mass % or more with respect to a total amount of the epoxy resin (A) and the hardener (B).

3. The ultrasonic vibrator according to claim 1, wherein a weight average molecular weight of the modified silicone (S) is 500 to 50000.

4. The ultrasonic vibrator according to claim 1, wherein an amount of the ion exchanger (C) is 0.25 to 10 parts by mass with respect to 100 parts by mass of a sum of the epoxy resin (A) and the hardener (B).

5. An ultrasonic endoscope comprising:
an insertion portion which is configured to be inserted into a body and is provided with an ultrasonic vibrator;
an operation portion connected to a proximal end of the insertion portion; and
a universal cord extending from the operation portion,
wherein the ultrasonic vibrator includes:
a piezoelectric element;
a backing material provided to be in contact with a first surface of the piezoelectric element;
an acoustic matching layer which has a first surface and a second surface, the first surface provided to be in contact with a second surface of the piezoelectric element and the backing material; and
an acoustic lens provided to be in contact with the second surface of the acoustic matching layer,
wherein the backing material is obtained by heating and molding a resin composition that includes:
an epoxy resin (A);
a hardener (B); and an ion exchanger (C),
wherein at least one of the epoxy resin (A) and the hardener (B) contains a modified silicone (S), and
wherein the epoxy resin (A) is at least one type selected from the group consisting of a bisphenol A type epoxy resin, a bisphenol F type epoxy resin, a phenol novolac type epoxy resin, and an epoxy-modified silicone.

6. The ultrasonic endoscope according to claim 5, wherein an amount of the modified silicone (S) is 10 mass % or more with respect to a total amount of the epoxy resin (A) and the hardener (B).

7. The ultrasonic endoscope according to claim 5, wherein a weight average molecular weight of the modified silicone (S) is 500 to 50000.

8. The ultrasonic endoscope according to claim 5, wherein an amount of the ion exchanger (C) is 0.25 to 10 parts by mass with respect to 100 parts by mass of a sum of the epoxy resin (A) and the hardener (B).

* * * * *